(12) United States Patent
Bauer et al.

(10) Patent No.: US 7,619,108 B2
(45) Date of Patent: Nov. 17, 2009

(54) PROCESS FOR PREPARING UNSATURATED ORGANOSILICON COMPOUNDS

(75) Inventors: Andreas Bauer, Simbach (DE); Juergen Pfeiffer, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 12/095,231

(22) PCT Filed: Nov. 22, 2006

(86) PCT No.: PCT/EP2006/068743

§ 371 (c)(1),
(2), (4) Date: May 28, 2008

(87) PCT Pub. No.: WO2007/063011

PCT Pub. Date: Jun. 7, 2007

(65) Prior Publication Data

US 2008/0293958 A1    Nov. 27, 2008

(30) Foreign Application Priority Data

Dec. 1, 2005    (DE)    .................. 10 2005 057 459

(51) Int. Cl.
*C07F 7/04* (2006.01)
(52) U.S. Cl. ..................................... 556/440
(58) Field of Classification Search ................. 556/440
See application file for complete search history.

(56) References Cited

U.S. PATENT DOCUMENTS

| | | | |
|---|---|---|---|
| 4,276,426 A | 6/1981 | Lindner et al. | |
| 4,927,948 A | 5/1990 | Bernhardt et al. | |
| 4,946,977 A | 8/1990 | Bernhardt et al. | |
| 6,815,554 B2 * | 11/2004 | Pfeiffer et al. | ............... 556/440 |
| 2002/0115878 A1 | 8/2002 | Wakita et al. | |
| 2002/0151736 A1 | 10/2002 | Pfeiffer et al. | |
| 2004/1071859 | 9/2004 | Pfeiffer | |

FOREIGN PATENT DOCUMENTS

| | | |
|---|---|---|
| DE | 28 51 456 C2 | 9/1982 |
| DE | 38 32 621 C1 | 9/1989 |
| DE | 103 08 579 B3 | 6/2004 |
| EP | 0 242 627 A2 | 10/1987 |
| EP | 0 437 653 B1 | 9/1994 |
| EP | 1 234 830 A2 | 8/2002 |
| EP | 1 249 454 A1 | 10/2002 |

OTHER PUBLICATIONS

Altmann et al., {Hydrolysis/Condensation Behavior of Alkoxy[(methacryloyloxy)alkyl]silanes: Structure-Reactivity Relations, Monatshefte fuer Chemie (2003), 134(8), 1081-1092}.*
DE 103 08 579 B3 corresponds to US 2004/171,859 A1.
EP 1 249 454 A corresponds to US 2002/151,736 A1.
EP 1 234 830 A2 corresponds to US 2002/115,878 A1.
DE 28 51 456 C2 corresponds to US 4,276,426.
DE 38 32 621 C1 corresponds to US 4,927,948.
EP 0 437 653 B1 corresponds to US 4,946,977.

* cited by examiner

*Primary Examiner*—Daniel M Sullivan
*Assistant Examiner*—Chukwuma O Nwaonicha
(74) *Attorney, Agent, or Firm*—Brooks Kushman P.C.

(57) ABSTRACT

Unsaturated organosilicon compounds are prepared by the reaction of a halo-functional organosilicon compound with a salt of an unsaturated carboxylic acid in the presence of a tertiary phosphine.

10 Claims, No Drawings

PROCESS FOR PREPARING UNSATURATED ORGANOSILICON COMPOUNDS

CROSS-REFERENCE TO RELATED APPLICATION

This application is the U.S. national phase of PCT Appln. No. PCT/EP2006/068743 filed Nov. 22, 2006 which claims priority to German application DE 10 2005 057 459.9 filed Dec. 1, 2005.

BACKGROUND OF THE INVENTION

1. Field of the Invention

The invention relates to a process for preparing unsaturated organosilicon compounds containing organic carbonyloxy groups in the presence of tertiary phosphines.

2. Description of the Related Art

Silicon compounds containing unsaturated organic carbonyloxy functions, e.g. 3-methacryloxypropyl-trimethoxysilane, are widely employed as bonding agents between inorganic and organic materials, e.g. in sizes for glass fibers, or as crosslinkers in organic polymers.

Various methods of preparing such compounds are known. Thus, for example, DE 2851456 C2 describes the hydrosilylation of chlorosilanes containing SiH bonds by means of unsaturated organic molecules such as allyl methacrylate in the presence of metal catalysts to form chlorosilanes containing corresponding unsaturated organic functional groups. The disadvantage of this process is the fact that the subsequent alcoholysis step necessary to obtain the corresponding alkoxy-functionalized silanes cannot be carried out continuously in most cases because of the high tendency of the unsaturated organic function to polymerize. Apart from this process, the direct reaction of an alkoxysilane containing SiH bonds with unsaturated organic molecules in the presence of metal catalysts is also known, e.g. from DE 38 32 621 C1. However, this process has the serious disadvantage that some of the alkoxysilanes necessary for carrying out the process are highly toxic and tend to decompose and therefore involve particular safety risks.

In the case of the processes described, for example, in EP 242 627 A2 and EP 437 653 B1, on the other hand, the compounds described are obtained by a nucleophilic substitution reaction between a metal or ammonium salt of an unsaturated organic acid and a haloorganofunctionalized silane. Here, the salt of the unsaturated organic acid is obtained in various ways. In the process described in EP 242 627 A2, the unsaturated organic acid is reacted with a tertiary amine to give the ammonium salt which can immediately be reacted in the same reaction vessel with the haloorganosilicon compound. However, a disadvantage is the low reactivity of the ammonium salts of unsaturated organic acids, which leads to very long reaction times and thus to a serious risk of polymerization of the product. Two alternative methods are described in EP 437 653 B1: in one process, the isolated sodium or potassium salt of the unsaturated organic acid is used. This has the disadvantage that this salt firstly has to be synthesized in a dedicated process and dried in a costly fashion. Alternatively, the metal salt of the unsaturated organic acid can be obtained by reaction of the corresponding metal alkoxide in the corresponding alcohol by reaction with the unsaturated organic acid. After addition of the haloorganofunctionalized silicon compound and removal of the alcohol by distillation, the reaction can then be carried out in the same reaction vessel. This process has the disadvantage that the metal alkoxides used are generally corrosive, highly reactive and very expensive and, in addition, large amounts of the respective, sometimes toxic, alcohol are required as solvent, which significantly reduces the attractiveness of this process. EP 1 249 454 A1 describes a process for preparing unsaturated organosilicon compounds having carbonyloxyorganic groups in the presence of phosphonium salts as phase transfer catalysts. The disadvantage of this process is that the catalysts used are very expensive and are usually solids, which makes their metering considerably more difficult.

SUMMARY OF THE INVENTION

In the search for a more cost-effective process, it has surprisingly been found that tertiary phosphines are extremely efficient phase transfer catalysts under the reaction conditions. These compounds are significantly cheaper than the corresponding phosphonium salts thereof and are also usually liquid, which makes implementation of the process on an industrial scale considerably easier.

DETAILED DESCRIPTION OF THE PREFERRED EMBODIMENTS

The invention thus provides a process for preparing unsaturated organosilanes containing organic carbonyloxy groups and having the formula $$(R^1O)_{3-n}R^2{}_nSi\text{—}X\text{—}OC(O)C(R^3)\!=\!CR^3{}_2 \qquad (I),$$

where $R^1$ may be identical or different and are each a monovalent, substituted or unsubstituted hydrocarbon radical which has from 1 to 10 carbon atoms and may be interrupted by oxygen atoms, $R^2$ may be identical or different and are each a monovalent, SiC-bonded, substituted or unsubstituted hydrocarbon radical which has from 1 to 10 carbon atoms and may be interrupted by oxygen atoms, or a sil(oxan)yl radical, X is a divalent, substituted or unsubstituted hydrocarbon radical which has from 1 to 40 carbon atoms and may be interrupted by oxygen atoms, $R^3$ may be identical or different and are each a hydrogen atom or a monovalent, substituted or unsubstituted hydrocarbon radical which has from 1 to 40 carbon atoms and may be interrupted by oxygen atoms, and n is 0, 1, 2 or 3, by reacting haloorganofunctional silicon compounds of the formula $$(R^1O)_{3-n}R^2{}_nSi\text{—}X\text{—}Y \qquad (II),$$

where $R^1$, $R^2$, X and n are as defined above and Y is a halogen atom, with a salt of an unsaturated organic carboxylic acid of the formula $$M^+[^-OC(O)C(R^3)\!=\!CR^3{}_2]_o \qquad (III),$$

where $R^3$ is as defined above, M is an alkali metal atom or alkaline earth metal atom and o can be 1 or 2 depending on the valence of M, in the presence of at least one tertiary phosphine of the general formula IV $$R^4{}_3P \qquad (IV)$$

where the radicals $R^4$ may be identical or different and are each a monovalent, substituted or unsubstituted hydrocarbon radical which has from 1 to 20 carbon atoms and may be interrupted by oxygen atoms and/or nitrogen atoms.

Examples of radicals $R^1$ are the radicals listed for radical $R^3$ which have from 1 to 10 carbon atoms.

$R^1$ is preferably a hydrocarbon radical which has from 1 to 10 carbon atoms, may be interrupted by oxygen atoms and may bear nitrogen, sulfur or phosphorus substituents, more preferably a methyl, ethyl, 2-methoxyethyl, phenyl or isopropyl radical, in particular an ethyl or methyl radical.

Examples of radical $R^2$ are the radicals listed for radical $R^3$ which have from 1 to 10 carbon atoms and also sil(oxan)yl radicals of the formula (V) $R_3Si-(OSiR_2)_p-$, where R may be identical or different and are each as defined for $R^1$, p is 0 or an integer from 1 to 100, with the proviso that the radicals R may be bound to the silicon atom either directly, i.e. SiC-bonded, or via oxygen.

The radical $R^2$ is preferably a hydrocarbon radical which has from 1 to 10 carbon atoms, may be interrupted by oxygen atoms and may bear nitrogen, sulfur or phosphorus substituents, or a sil(oxan)yl radical of the formula (V), more preferably a phenyl, ethyl, methyl or pentamethoxydisiloxyl radical, in particular a methyl or ethyl radical.

Examples of radical X are alkylene radicals such as the methylene, ethylene, n-propylene, isopropylene, n-butylene, isobutylene, tert-butylene, n-pentylene, isopentylene, neopentylene and tert-pentylene radicals; hexylene radicals such as the n-hexylene radical; heptylene radicals such as the n-heptylene radical; octylene radicals such as the n-octylene radical and isooctylene radicals such as the 2,2,4-trimethylpentylene radical; nonylene radicals such as the n-nonylene radical; decylene radicals such as the n-decylene radical; dodecylene radicals such as the n-dodecylene radical; octadecylene radicals such as the n-octadecylene radical; alkenylene radicals such as the vinylene and n-propenylene radicals; arylene radicals such as the phenylene, phenylmethylene, phenylethylene, 1-phenylpropylene and 2-phenylpropylene radicals, and also (poly)alkylenoxy groups of the formula (VI) $-(CH_2)_q(OZ)_m-$, where m is an integer from 1 to 100, q is an integer from 1 to 6 and Z is an ethylene, n-propylene, isopropylene, n-butylene or isobutylene radical.

X is preferably a divalent hydrocarbon radical which has from 1 to 10 carbon atoms, may be interrupted by oxygen atoms and may be substituted by nitrogen, sulfur or phosphorus, more preferably an n-propylene, isopropylene, n-butylene, isobutylene, methylene, ethylene or p-phenylene radical, and most preferably a methylene or n-propylene radical.

Examples of substituted or unsubstituted hydrocarbon radicals $R^3$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as o-, m-, and p-tolyl radicals, xylyl radicals and ethylphenyl radicals; and aralkyl radicals such as the benzyl radical, and the α- and β-phenylethyl radicals; and also dialkylaminoalkyl radicals such as the dimethylaminomethyl, 2-dimethylaminoethyl and 2-dimethylaminopropyl radicals.

The radical $R^3$ is preferably a hydrogen atom or a hydrocarbon radical which has from 1 to 10 carbon atoms, may be interrupted by oxygen atoms and may bear nitrogen, sulfur or phosphorus substituents, more preferably a hydrogen atom or a methyl or ethyl radical, in particular a hydrogen atom or a methyl radical.

n is preferably 0 or 1.

Y is preferably an iodine, bromine or chlorine atom, more preferably a chlorine atom.

Examples of M are alkali metal atoms, e.g. Li, Na, K and Rb, and alkaline earth metal atoms, e.g. Mg, Ca, Sr and Ba.

M is preferably sodium or potassium, in particular potassium.

When M is an alkali metal atom, o in the formula (III) is 1, and when M is an alkaline earth metal atom, o is 2.

Examples of unsaturated organosilanes of the formula (I) which contain organic carbonyloxy groups and can be prepared by the process of the invention are acryloxymethyltrimethoxysilane, acryloxymethyltriethoxysilane, acryloxymethyltriphenoxysilane, acryloxymethyltris(2-methoxyethoxy)silane, acryloxymethyltriisopropoxysilane, acryloxymethyl(dimethoxy)methylsilane, acryloxymethyl(diethoxy)methylsilane, acryloxymethyl(diphenoxy)methylsilane, acryloxymethylbis(2-methoxyethoxy)methylsilane, acryloxymethyl(diisopropoxy)methylsilane, acryloxymethyl(dimethyl)methoxysilane, acryloxymethyl(dimethyl)ethoxysilane, acryloxymethyl(dimethyl)phenoxysilane, acryloxymethyl(dimethyl)(2-methoxyethoxy)silane, acryloxymethyl(dimethyl)isopropoxysilane, methacryloxymethyltrimethoxysilane, methacryloxymethyltriethoxysilane, methacryloxymethyltriphenoxysilane, methacryloxymethyltris(2-methoxyethoxy)silane, methacryloxymethyltriisopropoxysilane, methacryloxymethyl(dimethoxy)methylsilane, methacryloxymethyl(diethoxy)methylsilane, methacryloxymethyl(diphenoxy)methylsilane, methacryloxymethylbis(2-methoxyethoxy)methylsilane, methacryloxymethyl(diisopropoxy)methylsilane, methacryloxymethyl(dimethyl)methoxysilane, methacryloxymethyl(dimethyl)ethoxysilane, methacryloxymethyl(dimethyl)phenoxysilane, methacryloxymethyl(dimethyl)(2-methoxyethoxy)silane, methacryloxymethyl(dimethyl)isopropoxysilane, 3-acryloxypropyltrimethoxysilane, 3-acryloxypropyltriethoxysilane, 3-acryloxypropyltriphenoxysilane, 3-acryloxypropyltris(2-methoxyethoxy)silane, 3-acryloxypropyltriisopropoxysilane, 3-acryloxypropyl(dimethoxy)methylsilane, 3-acryloxypropyl(diethoxy)methylsilane, 3-acryloxypropyl(diphenoxy)methylsilane, 3-acryloxypropylbis(2-methoxyethoxy)methylsilane, 3-acryloxypropyl(diisopropoxy)methylsilane, 3-acryloxypropyl(dimethyl)methoxysilane, 3-acryloxypropyl(dimethyl)ethoxysilane, 3-acryloxypropyl(dimethyl)phenoxysilane, 3-acryloxypropyl(dimethyl)(2-methoxyethoxy)silane, 3-acryloxypropyl(dimethyl)isopropoxysilane, 3-methacryloxypropyltrimethoxysilane, 3-methacryloxypropyltriethoxysilane, 3-methacryloxypropyltriphenoxysilane, 3-methacryloxypropyltris(2-methoxyethoxy)silane, 3-methacryloxypropyltriisopropoxysilane, 3-methacryloxypropyl(dimethoxy)methylsilane, 3-methacryloxypropyl(diethoxy)methylsilane, 3-methacryloxypropyl(diphenoxy)methylsilane, 3-methacryloxypropylbis(2-methoxyethoxy)methylsilane, 3-methacryloxypropyl(diisopropoxy)methylsilane, 3-methacryloxypropyl(dimethyl)methoxysilane, 3-methacryloxypropyl(dimethyl)ethoxysilane, 3-methacryloxypropyl(dimethyl)

phenoxysilane, 3-methacryloxypropyl(dimethyl)(2-methoxyethoxy)silane and 3-methacryloxypropyl(dimethyl)isopropoxysilane.

Examples of haloorganofunctional silicon compounds of the formula (II) used in the process of the invention are chloromethyltrimethoxysilane, bromomethyltrimethoxysilane, chloromethyltriethoxysilane, bromomethyltriethoxysilane, chloromethyltriphenoxysilane, bromomethyltriphenoxysilane, chloromethyltris(2-methoxyethoxy)silane, bromomethyltris(2-methoxyethoxy)silane, chloromethyltriisopropoxysilane, bromomethyltriisopropoxysilane, chloromethyl(dimethoxy)methylsilane, bromomethyl(dimethoxy)methylsilane, chloromethyl(diethoxy)methylsilane, bromomethyl(diethoxy)methylsilane, chloromethyl(diphenoxy)methylsilane, bromomethyl(diphenoxy)methylsilane, chloromethylbis(2-methoxyethoxy)methylsilane, bromomethylbis(2-methoxyethoxy)methylsilane, chloromethyl(diisopropoxy)methylsilane, bromomethyl(diisopropoxy)methylsilane, chloromethyl(dimethyl)methoxysilane, bromomethyl(dimethyl)methoxysilane, chloromethyl(dimethyl)ethoxysilane, bromomethyl(dimethyl)ethoxysilane, chloromethyl(dimethyl)phenoxysilane, bromomethyl(dimethyl)phenoxysilane, chloromethyl(dimethyl)(2-methoxyethoxy)silane, bromomethyl(dimethyl)(2-methoxyethoxy)silane, chloromethyl(dimethyl)isopropoxysilane, bromomethyl(dimethyl)isopropoxysilane, 3-chloropropyltrimethoxysilane, 3-bromopropyltrimethoxysilane, 3-chloropropyltriethoxysilane, 3-bromopropyltriethoxysilane, 3-chloropropyltriphenoxysilane, 3-bromopropyltriphenoxysilane, 3-chloropropyltris(2-methoxyethoxy)silane, 3-bromopropyltris(2-methoxyethoxy)silane, 3-chloropropyltriisopropoxysilane, 3-bromopropyltriisopropoxysilane, 3-chloropropyl(dimethoxy)methylsilane, 3-bromopropyl(dimethoxy)methylsilane, 3-chloropropyl(diethoxy)methylsilane, 3-bromopropyl(diethoxy)methylsilane, 3-chloropropyl(diphenoxy)methylsilane, 3-bromopropyl(diphenoxy)methylsilane, 3-chloropropylbis(2-methoxyethoxy)methylsilane, 3-bromopropylbis(2-methoxyethoxy)methylsilane, 3-chloropropyl(diisopropoxy)methylsilane, 3-bromopropyl(diisopropoxy)methylsilane, 3-chloropropyl(dimethyl)methoxysilane, 3-bromopropyl(dimethyl)methoxysilane, 3-chloropropyl(dimethyl)ethoxysilane, 3-bromopropyl(dimethyl)ethoxysilane, 3-chloropropyl(dimethyl)phenoxysilane 3-bromopropyl(dimethyl)phenoxysilance, 3-chloropropyl(dimethyl)(2-methoxyethoxy)silane, 3-bromopropyl(dimethyl)(2-methoxyethoxy)silane, 3-chloropropyl(dimethyl)isopropoxysilane, 3-bromopropyl(dimethyl)isopropoxysilane.

The silicon compound of the formula (II) used according to the invention is preferably chloromethyltrimethoxysilane, chloromethyltriethoxysilane, chloromethyl(dimethoxy)methylsilane, chloromethyl(diethoxy)methylsilane, chloromethyl(dimethyl)methoxysilane, chloromethyl(dimethyl)ethoxysilane, 3-chloropropyltrimethoxysilane, 3-chloropropyltriethoxysilane, 3-chloropropyl(dimethoxy)methylsilane, 3-chloropropyl(diethoxy)methylsilane, 3-chloropropyl(dimethyl)methoxysilane and 3-chloropropyl(dimethyl)ethoxysilane, with particular preference being given to chloromethyltrimethoxysilane, chloromethyl(dimethoxy)methylsilane, 3-chloropropyltriethoxysilane, 3-chloropropyltrimethoxysilane, and 3-chloropropyl(dimethoxy)methylsilane.

The haloorganofunctional silicon compounds of the formula (II) used in the process of the invention are commercial products or can be prepared by methods customary in chemistry.

Examples of the salts of an unsaturated organic carboxylic acid of the formula (III) used in the process of the invention are potassium acrylate, potassium methacrylate, sodium acrylate, sodium methacrylate, potassium trans-but-2-enoate, potassium cis-but-2-enoate, sodium trans-but-2-enoate, sodium cis-but-2-enoate, potassium trans-2-methylbut-2-enoate, potassium cis-2-methylbut-2-enoate, sodium trans-2-methylbut-2-enoate and sodium cis-2-methylbut-2-enoate.

The salts of the formula (III) used in the process of the invention are commercial products or can be prepared by methods customary in chemistry.

Examples of substituted or unsubstituted hydrocarbon radicals $R^4$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and 2-propenyl radicals; (substituted or unsubstituted) aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical, and the α- and β-phenylethyl radicals.

Preference is given to using one tertiary phosphine, although any mixtures of different tertiary phosphines can also be used. Particularly preferred examples of the tertiary phosphines of the general formula (IV) used in the process of the invention are tributylphosphine, trioctylphosphine and triphenyl-phosphine.

The tertiary phosphines of the formula (IV) used in the process of the invention are commercial products or can be prepared by methods customary in chemistry.

The reaction according to the invention of the salt of the unsaturated organic acid of the formula (III) with a haloorganofunctional silicon compound of the formula (II) is preferably carried out at temperatures of from 60 to 150° C., more preferably from 70 to 120° C., and preferably at a pressure of from 100 to 1000 hPa, more preferably from 200 to 300 hPa.

In the process of the invention, the molar ratio of the salt of the formula (III) to the haloorganofunctional silicon compound of the formula (II) is preferably from 0.5 to 1.5, more preferably from 0.9 to 1.1, and in particular from 1 to 1.05.

The process of the invention can be carried out in air or under an inert gas atmosphere. For the present purposes, an inert gas is a gas which is unreactive toward the components present in the reaction mixture under the prevailing reaction conditions, e.g. nitrogen or argon or a mixture thereof. The process is preferably carried out under an inert gas atmosphere, more preferably under a nitrogen atmosphere. If desired, the reaction according to the invention can also be carried out under a nitrogen atmosphere containing from 0.1 to 2 percent of oxygen.

The process of the invention is preferably carried out in the substantial absence of traces of water, which can be achieved by customary methods for removing traces of water from the components present in the reaction vessel, for example by drying of the organic solvent or the inert gas atmosphere, etc.

In the process of the invention, the tertiary phosphine is preferably used in an amount of from 0.1 to 20 mol percent, more preferably from 0.5 to 10 mol percent, and in particular from 1 to 5 mol percent, in each case based on the amount of the haloorganofunctional silicon compound of the formula (II) used.

The reaction according to the invention of the haloorganofunctional compound of the formula (II) with the salts of the formula (III) can be carried out in the presence or absence of an organic solvent, but preference is given to using an organic solvent, in particular a polar aprotic solvent.

If an organic solvent is used in the process of the invention, it is preferably used in an amount of from 5 to 300 percent by weight, more preferably from 10 to 100 percent by weight, and in particular from 20 to 50 percent by weight, in each case based on the amount of haloorganic silicon compound of the formula (II) used.

Examples of organic, polar aprotic solvents which can be used in the process of the invention are ones which aid the reaction according to the invention, for instance acetone, N,N-dimethylformamide, dimethyl sulfoxide, N-methyl-2-pyrrolidone, γ-butyrolactone, diethylene glycol dimethyl ether and diethylene glycol diethyl ether, with preference being given to acetone, N,N-dimethylformamide and N-methyl-2-pyrrolidone, particularly preferably N,N-dimethylformamide.

If desired, the process of the invention can be carried out in the presence of inhibitors, i.e. compounds which prevent the undesirable polymerization of the target compounds via the unsaturated organic function. Preference is given to using inhibitors in the process of the invention.

Examples of inhibitors which can be used in the process of the invention are aromatic amines, quinones, hydroquinones, sterically hindered phenols or stable free radicals, e.g. N,N'-diphenyl-p-phenylenediamine, N,N'-di-β-naphthyl-p-phenylenediamine, phenothiazine, hydroquinone, hydroquinone monomethyl ether, 2,6-di-tert-butylphenol, 2,6-di-tert-butyl-4-methylphenol, 2,6-di-tert-butyl-4-(N,N-dimethylamino) methylphenol and 2,2,6,6-tetramethylpiperidyl N-oxide. These can be used individually or as mixtures.

If inhibitors are used in the process of the invention, they are preferably used in amounts of preferably from 0.01 to 1% by weight, more preferably from 0.05 to 0.4% by weight, in each case based on the amount of the haloorganofunctionalized silicon compound of the formula (II) used.

Apart from haloorganofunctional silicon compounds of the formula (II), salts of an unsaturated organic carboxylic acid of the formula (III), tertiary phosphines of the formula (IV), if desired a polar aprotic organic solvent and if desired an inhibitor, it is also possible to use further additives customary for nucleophilic substitution reactions in the process of the invention. Examples of such customary additives are alkali metal iodides. Otherwise, preference is given to using no further materials.

The components used in the process of the invention can in each case be one type of such a component or a mixture of at least two types of a respective component.

In the process of the invention, the components used can be mixed with one another in any order.

After the reaction according to the invention is complete, the resulting unsaturated organosilicon compounds containing organic carbonyloxy groups can be isolated and purified by methods known per se, e.g. by filtration or centrifugation to remove the metal halide formed, distillation, rectification, thin film distillation, etc.

The resulting unsaturated organosilicon compounds containing organic carbonyloxy groups can be used for all purposes for which such compounds have been used hitherto.

In a preferred embodiment of the process of the invention, haloorganofunctional silicon compounds of the formula (II) are reacted with a salt of an unsaturated organic carboxylic acid of the formula (III) in the presence of tertiary phosphines of the formula (IV), a polar aprotic organic solvent and an inhibitor.

The process of the invention can be carried out batchwise or continuously.

The process of the invention has the advantage that it is simple to carry out and enables unsaturated organosilicon compounds containing organic carbonyloxy groups to be prepared in a more efficient and inexpensive manner compared to the prior art.

The process of the invention has the particular advantage that the use of tertiary phosphines results in formation of no decomposition products during the reaction, which makes obtaining a highly pure product significantly easier.

The process of the invention has the further advantage that the use of tertiary phosphines in combination with the use of polar aprotic solvents makes it possible to obtain the target products of the formula (I) in an exceptionally short time under very mild conditions.

Furthermore, all solvents used in the process of the invention can be reused, which results in an environmentally friendly process with particularly sparing utilization of resources.

In the following examples, all parts and percentages are, unless indicated otherwise, by weight. Unless indicated otherwise, the following examples are carried out at the pressure of the surrounding atmosphere, i.e. at about 1 000 hPa, and at room temperature, i.e. about 20° C., or a temperature which is established on combining the reactants at room temperature without additional heating or cooling. All viscosities reported in the examples are at a temperature of 25° C. All reactions described in the examples were carried out under an inert gas atmosphere comprising nitrogen.

EXAMPLE 1

170.7 g (1 mol) of chloromethyltrimethoxysilane, 6.1 g (0.03 mol) of tri-n-butylphosphine and 0.1 g (0.05 mol % based on silane) of phenothiazine are placed in a reaction vessel at 90° C. and 130.4 g (1.05 mol) of potassium methacrylate are added a little at a time over a period of 1 hour. After stirring at 90° C. for another 2 hours, the reaction is complete. After filtration from the potassium chloride formed, the product is distilled by means of a short-path evaporator, giving 207.1 g (94%) of methacryloxymethyltrimethoxysilane having a purity of 98.5%.

EXAMPLE 2

Using a method analogous to Example 1, 212.7 g (1 mol) of chloromethyltriethoxysilane are reacted in the presence of 6.1 g (0.03 mol) of tri-n-butylphosphine and 0.1 g of phenothiazine with 130.4 g (1.05 mol) of potassium methacrylate at 90° C. The reaction is complete 4 hours after all the potassium methacrylate has been introduced. Work-up gives 250.0 g (95%) of methacryloxymethyltriethoxysilane having a purity of 99.0%.

EXAMPLE 3

Using a method analogous to Example 1, 198.7 g (1 mol) of 3-chloropropyltrimethoxysilane are reacted in the presence of 6.1 g (0.03 mol) of tri-n-butylphosphine and 0.1 g of phenothiazine with 130.4 g (1.05 mol) of potassium methacrylate at 90° C. The reaction is complete 10 hours after all the potassium methacrylate has been introduced. Work-up gives 221.0 g (89%) of 3-methacryloxypropyltrimethoxysilane having a purity of 98.3%.

EXAMPLE 4

170.7 g (1 mol) of chloromethyltrimethoxysilane, 11.1 g (0.03 mol) of tri-n-octylphosphine and 0.1 g (0.05 mol % based on silane) of phenothiazine are placed in a reaction vessel at 90° C. and 130.4 g (1.05 mol) of potassium methacrylate are added a little at a time over a period of 1 hour. After stirring at 90° C. for another 1 hour, the reaction is complete. After filtration from the potassium chloride formed, the product is distilled by means of a short-path evaporator, giving 209.3 g (95%) of methacryloxymethyltrimethoxysilane having a purity of 98.8%.

EXAMPLE 5

Using a method analogous to Example 4, 212.7 g (1 mol) of chloromethyltriethoxysilane are reacted in the presence of 11.1 g (0.03 mol) of tri-n-butylphosphine and 0.1 g of phenothiazine with 130.4 g (1.05 mol) of potassium methacrylate at 90° C. The reaction is complete 3 hours after all the potassium methacrylate has been introduced. Work-up gives 244.7 g (93%) of methacryloxymethyltriethoxysilane having a purity of 99.2%.

EXAMPLE 6

Using a method analogous to Example 1, 198.7 g (1 mol) of 3-chloropropyltrimethoxysilane are reacted in the presence of 6.1 g (0.03 mol) of tri-n-butylphosphine and 0.1 g of phenothiazine with 130.4 g (1.05 mol) of potassium methacrylate at 90° C. The reaction is complete 9 hours after all the potassium methacrylate has been introduced. Work-up gives 226.0 g (91%) of 3-methacryloxypropyltrimethoxysilane having a purity of 98.3%.

EXAMPLE 7

170.7 g (1 mol) of chloromethyltrimethoxysilane, 7.9 g (0.03 mol) of triphenylphosphine and 0.1 g (0.05 mol % based on silane) of phenothiazine are placed in a reaction vessel at 90° C. and 130.4 g (1.05 mol) of potassium methacrylate are added a little at a time over a period of 1 hour. After stirring at 90° C. for another 6 hours, the reaction is complete. After filtration from the potassium chloride formed, the product is distilled by means of a short-path evaporator, giving 193.9 g (95%) of methacryloxymethyl-trimethoxysilane having a purity of 98.4%.

What is claimed is:

1. A process for preparing unsaturated organosilanes containing organic carbonyloxy groups and having the formula $$(R^1O)_{3-n}R^2{}_nSi-X-OC(O)C(R^3)=CR^3{}_2 \quad (I),$$

where
$R^1$ are identical or different monovalent, substituted or unsubstituted $C_{1-10}$ hydrocarbon radicals optionally interrupted by oxygen atoms,
$R^2$ are identical or different monovalent, SiC-bonded, substituted or unsubstituted $C_{1-10}$ hydrocarbon radicals optionally interrupted by oxygen atoms or a sil(oxan)yl radical,
X each are divalent, substituted or unsubstituted $C_{1-40}$ hydrocarbon radicals optionally interrupted by oxygen atoms, $R^3$ are identical or different and are a hydrogen atom or a monovalent, substituted or unsubstituted $C_{1-40}$ hydrocarbon radical optionally interrupted by oxygen atoms, and n is 0, 1, 2 or 3, comprising reacting haloorganofunctional silicon compounds of the formula $$(R^1O)_{3-n}R^2{}_nSi-X-Y \quad (II),$$

where Y is a halogen atom, with a salt of an unsaturated organic carboxylic acid of the formula $$M[OC(O)C(R^3)=CR^3{}_2]_o \quad (III),$$

where
$R^3$ is as defined above, M is an alkali metal atom or alkaline earth metal atom and o is 1 or 2 depending on the valence of M, in the presence of at least one tertiary phosphine of the formula IV $$R^4{}_3P \quad (IV)$$

where
the radicals $R^4$ are identical or different monovalent $C_{1-20}$ hydrocarbon radicals.

2. The process of claim 1, wherein at least one tertiary phosphine is selected from the group consisting of tributylphosphine, trioctylphosphine, and triphenylphosphine.

3. The process of claim 1, wherein the molar ratio of the salt of formula (III) to the haloorganofunctional silicon compound of the formula (II) is from 0.5 to 1.5.

4. The process of claim 2, wherein the molar ratio of the salt of formula (III) to the haloorganofunctional silicon compound of the formula (II) is from 0.5 to 1.5.

5. The process of claim 1, wherein the process is carried out under an inert gas atmosphere.

6. The process of claim 1, wherein tertiary phosphines are used in an amount of from 0.5 to 10 percent by weight, based on the amount of the haloorganofunctional silicon compound of the formula (II).

7. The process of claim 1, wherein the salt of the formula (III) which is used is obtained by reacting an aqueous solution of a metal hydroxide (i) of the formula (VII) $M(OH)_k$, where k is 1 or 2 depending on the valence of M, with an unsaturated organic carboxylic acid (ii) of the formula $$HOC(O)C(R^3)=CR^3{}_2 \quad (IV),$$

in the presence of an organic solvent (iii) which forms an azeotrope with water and forms a two-phase system with water in the liquid state, followed by a) removing water by azeotropic distillation, and b) separating from 10 to 100% by weight of the organic solvent by distillation.

8. The process of claim 1, which is carried out in the presence of an organic solvent.

9. The process of claim 1, wherein haloorganofunctional silicon compounds of the formula (II) are reacted with a salt of an unsaturated organic carboxylic acid of the formula (III) in the presence of at least one tertiary phosphine, a polar aprotic organic solvent and an inhibitor.

10. The process of claim 1, wherein haloorganofunctional silicon compounds of the formula (II) are reacted with a salt of an unsaturated organic carboxylic acid of the formula (III) in the presence of at least one tertiary phosphine, a polar aprotic organic solvent and an inhibitor, where the salt of the formula (III) is prepared by reacting an aqueous solution of a metal hydroxide (i) of the formula (VII) with an unsaturated organic carboxylic acid (ii) of the formula (IV) in the presence of an organic solvent (iii) which forms an azeotrope with water and forms a two-phase system with water in the liquid state, followed by a) removing the water by azeotropic distillation and b) separating from 10 to 100% by weight of the organic solvent used by distillation.

* * * * *